United States Patent [19]

Tyndall et al.

[11] Patent Number: 5,449,618

[45] Date of Patent: Sep. 12, 1995

[54] METHODS OF DEGRADING NAPALM B

[75] Inventors: Richard L. Tyndall, Clinton; Arpad Vass, Oak Ridge, both of Tenn.

[73] Assignee: Martin Marietta Energy Systems, Inc., Oak Ridge, Tenn.

[21] Appl. No.: 168,603

[22] Filed: Dec. 16, 1993

Related U.S. Application Data

[63] Continuation-in-part of Ser. No. 11,841, Feb. 1, 1993, Pat. No. 5,314,824, and a continuation of Ser. No. 693,998, Apr. 26, 1991, abandoned.

[51] Int. Cl.[6] .................. C12S 13/00; B09B 3/00; C12P 1/04; C12P 39/00
[52] U.S. Cl. .................. 435/262.5; 435/262; 435/170; 435/42; 435/243; 588/203
[58] Field of Search .............. 435/262, 262.5, 264, 435/41, 42, 170, 253.3, 829, 874, 243; 588/203

[56] References Cited

U.S. PATENT DOCUMENTS

| | | | |
|---|---|---|---|
| 2,867,945 | 1/1959 | Gottas et al. | 47/58 |
| 3,914,164 | 10/1975 | Clark | 204/149 |
| 4,127,447 | 11/1978 | Griffith et al. | 195/116 |
| 4,391,887 | 7/1983 | Baumgarten | 435/42 |
| 4,401,569 | 8/1983 | Jhaveri et al. | 210/610 |
| 4,447,541 | 5/1984 | Peterson | 435/264 |
| 4,511,657 | 4/1985 | Colaruotolo et al. | 435/253 |
| 4,535,061 | 8/1985 | Chakrabarty et al. | 435/253 |
| 4,664,805 | 5/1987 | Focht | 210/611 |
| 4,713,340 | 12/1987 | Crawford | 435/253 |
| 4,713,343 | 12/1987 | Wilson et al. | 435/264 |
| 4,737,461 | 4/1988 | Sugisawa et al. | 435/200 |
| 4,803,166 | 2/1989 | Kulpa et al. | 435/253.3 |
| 4,804,629 | 2/1989 | Roy | 435/253.3 |
| 4,816,403 | 3/1989 | Roy | 435/253.3 |
| 4,833,086 | 5/1989 | Horowitz | 435/252.1 |
| 4,853,334 | 8/1989 | Vanderbergh et al. | 435/262 |
| 4,859,594 | 8/1989 | Portier | 435/172.1 |
| 4,877,736 | 10/1989 | Fliermans | 435/183 |
| 5,314,821 | 5/1994 | Tyndall | 435/252.1 |

OTHER PUBLICATIONS

*Merck Index*, 9th Ed. Rahway, N.J., 1976, p. 827.

S. B. Garland et al "The Use of Methanotrophic Bacteria for the Treatment of Groundwater Contaminated with Trichloroethene at the U.S. Department of Energy Kansas City Plant," ORNL/TM-11084, Nov. 1989, pp. 21, 41.

R. L. Tyndall et al "Isolation of Amoebic-Bacterial Consortia Capable of Degrading Trichloroethylene," Twelfth Sym. on Biotech. for Fuels and Chemicals, May 7, 1990.

A. A. Vass et al, "Isolating Free Living Amoeba Can Select for Complex, Stable Consortia Capable of Degrading Toxins," ASM Int.Conf. on Multicellular Behavior of Bacteria, Oct. 21, 1990.

Stanier, et al. "The Microbial World" Prentice Hall, 1986 pp. 574–575.

Tyndall, et al. "Free-Living Amoebae Used To Isolate Consortia Capable of Degrading Trichloroethylene" *Applied Biochemistry and Biotechnology*, vol. 28/29, 1991, pp. 917–925.

Hall, et al. BIOSIS Abstract 85:343756, 1985.

*Primary Examiner*—William H. Beisner
*Assistant Examiner*—Timothy J. Reardon
*Attorney, Agent, or Firm*—J. A. Marasco; H. W. Adams

[57] ABSTRACT

Methods of degrading napalm and/or trinitrotoluene involve contacting the waste with specific intra-amoebic isolates of ATCC 40908 and/or dispersants derived therefrom. Useful isolates include is deposited as ATCC 77529, NAP-1 deposited as ATCC 77526 and 13 deposited as ATCC 77527.

9 Claims, No Drawings

METHODS OF DEGRADING NAPALM B

The United States Government has rights in this invention pursuant to contract No. DE-AC05-84OR21400 between the United States Department of Energy and Martin Marietta Energy Systems, Inc.

CROSS-REFERENCE TO RELATED APPLICATIONS

This application is a continuation-in-part of application Ser. No. 08/011,841, filed on Feb. 1, 1993, now U.S. Pat. No. 5,314,821, issued on May 24, 1994, entitled *Amoeba/Bacteria Consortia and Uses for Degrading Wastes and Contaminants*, the entire disclosure of which is incorporated herein by reference application Ser. No. 08/011,841 is a continuation of application Ser. No. 07/693,998, filed on Apr. 26, 1991, now abandoned.

FIELD OF THE INVENTION

The present invention relates to methods of biological degradation of napalm and trinitrotoluene (TNT), and more particularly to such methods which utilize intra-amoebic isolates. Napalm, as used herein, is defined as Napalm B, a mxiture of gasoline, benzene, and polystyrene. The original, obsolete napalm formula, containing napthenic and palmitic acids, has not been tested.

BACKGROUND OF THE INVENTION

The end of the "cold war" has brought about the need for the reduction or elimination of many weapons stockpiles. Among those are explosives and incendiaries which, for the sake of protecting the environment, can no longer be burned. Therefore there is a need for alternative methods for eliminating explosives and incendiaries, in particular, waste napalm and TNT.

OBJECTS OF THE INVENTION

Accordingly, it is an object of the present invention to provide a new and improved method of biological degradation of napalm.

It is another object of the present invention to provide a new and improved method of biological degradation of TNT.

Further and other objects of the present invention will become apparent from the description contained herein.

SUMMARY OF THE INVENTION

In accordance with one aspect of the invention, the foregoing and other objects are achieved by a method of degrading napalm which involves the steps of:

a. providing a culture of a bacterium which comprises an intra-amoebic isolate essentially identical to American Type Culture Collection Deposit Number 77529, a mutant thereof possessing all the identifying characteristics thereof, or mixtures thereof;

b. deriving an aqueous dispersant solution from the culture;

c. contacting napalm B with a sufficient amount of the dispersant solution to emulsify the napalm B; and, d. contacting the emulsified napalm B with a sufficient amount of at least one of intraamoebic isolates essentially identical to American Type Culture Collection Deposit Numbers 77526 and 77527, a mutant thereof possessing all the identifying characteristics thereof, or mixtures thereof, to degrade the emulsified napalm B.

DETAILED DESCRIPTION OF THE INVENTION

Amoeba/bacteria consortium 46, ATCC Deposit Reference No. 40908, was found to contain certain useful bacteria, designated as intra-amoebic isolates 13, NAP-1, 1S and CR-1. Isolate 1S produces a biodispersant which separates the components of napalm, and also elutes TNT bound to soil. Isolates NAP-1 and 13, in combination with the biodispersant produced from isolate 1S, degrade and disperse the polystyrene component of napalm. Isolate CR-1 degrades TNT in a manner which renders it undetectable by standard analysis methods.

The method of deriving a dispersant and using it to separate components of napalm is described in general terms as follows: Isolate 1S is usually grown on culture plates containing a solid medium. A typical solid medium suitable for this purpose comprises 15g/L Bacto Tryptone (Pancreatic Digest of Casein), 5g/L Bacto Soytone (Papaic Digest of Soybean Meal), 5g/L Sodium Chloride and 15g/L Bacto Agar. Small amounts of freshly grown bacteria (typically 1-3 day old cultures) are spread on the surface of the solid medium and incubated at a temperature of about 15° C. to about 40° C., preferably about 30° C., for several days (usually about 3-5 days) in an aerobic environment. When growth is sufficiently heavy, the bacteria are harvested, washed by centrifugation (usually about three times) with normal saline (about 8.5g/L NaCl), diluted (to about 10 ml for each culture plate used) with normal saline, and autoclaved (typically for about 15 minutes at 121° C. at 15 psi). The autoclaved solution is allowed to cool, and is preferably filtered through a 0.2$\mu$m nucleopore filter to remove extraneous membranes and other bacterial debris. The biodispersant solution thus derived is preferably stored in a sterile container. The biodispersant solution is preferably diluted 1:10 with sterile distilled water for use in separation of napalm components.

Napalm typically composed of polystyrene, leaded gasoline, and benzene, is degraded as follows: Napalm, preferably in its liquid form, is added to the diluted biodispersant solution. The mixture should generally contain about 5% to about 25%, preferably about 10%, napalm. Upon thorough mixing, an emulsifying effect is observed in the mixture, indicating suspension of the polystyrene component of the napalm.

To further degrade the mixture, a supernatant bacterial preparation containing about $10^3$/ml to about $10^8$/ml, usually about $10^5$/ml, isolate 13 and/or isolate NAP-1, preferably both, is added to the emulsified mixture in a ratio of about 3:1 to about 1:3, preferably about 1:1. The mixture is then incubated at a temperature of about 15° C. to about 40° C., preferably about 30° C., until the polystyrene component of the napalm has dissolved, usually at least 24 hours. Marked increases in breakdown products of polystyrene, indicative of its degradation, will be evident, as seen in Table 1.

EXAMPLE

A dispersant was derived from Isolate 1S as described hereinabove, and was mixed with napalm as described hereinabove to produce an emulsified mixture containing a suspension of the polystyrene component of the napalm. Results are shown in Table 1.

EXAMPLE II

Isolate 13 and isolate NAP-1 were grown separately on Trypticase Soy Agar at 30° C. for 3 days and harvested dry. The bacteria were prepared and used as described hereinabove to degrade the mixture produced in Example I. Results are shown in Table 1.

TABLE 1

Effect of Isolates 13 and Nap-1 on Volatile Aromatic Components of Napalm

|  | Water Control | Bio-dispersant | Biodispersant + Isolates 13, NAP-1 |
|---|---|---|---|
| Benzene in: | | | |
| Polystyrene[a] | 37,000,000 | 28,000,000 | 38,000,000 |
| Supernate[b] | 140,000 | 320,000 | 110,000 |
| Ethyl Benzene in: | | | |
| Polystyrene | 80,000 | 80,000 | 150,000 |
| Supernate | 420 | 620 | 150,000 |
| Toluene in: | | | |
| Polystyrene | 81,000 | 91,000 | 130,000 |
| Supernate | 1,800 | 2,400 | 210,000 |
| Total xylene in: | | | |
| Polystyrene | 180,000 | 150,000 | 280,000 |
| Supernate | 1,200 | 820 | 260,000 |

[a] $\mu g/kg$ (semi solid portion of mixture)
[b] $\mu g/L$ (liquid portion of mixture)

A general, simple method of treating soil contaminated with TNT is described as follows. Soil contaminated with TNT is loaded into a vessel, usually a column, for contacting the soil with a biodispersant. An aqueous solution containing biodispersant derived from isolate 1 S (as described hereinabove) is added and allowed to percolate down through the soil and elute the TNT. The solution may be forced through the soil, the soil may be pretreated, and/or other process steps known to the skilled artisan may be taken to increase the efficiency of the process. The process may be carried out at about room temperature, but process temperature is not a particularly critical factor.

EXAMPLE III 10 grams of contaminated soil were loaded into two columns, 7 in. in height with a diameter of 2.0 inches, each column having a Whatman #1 filter pad in the bottom thereof to retain the soil. One column was eluted with 100 ml distilled, deionized water, and the other column was eluted with 100 ml of the above described dispersant solution. The flow rate through the soil was slow, requiring 12 hours for all the liquid to pass through the columns. The eluate and soil for both the control and test columns were collected and analyzed for TNT and metabolites after acetonitrile extraction. No metabolites were detected. The results are shown in Table 2, indicating a significant reduction in detectable TNT in the soil eluted with the biodispersant solution.

TABLE 2

Desorption of TNT from Soil Using Biodispersants from Isolate 1S

|  | VA Site (soil) | NJ Site (soil) | NJ Site (eluate) |
|---|---|---|---|
| Water Control | 5,900 μg/g | 370 μg/g | 15,750 μg/L |
| 10% Biodispersant | 1,900 μg/g | 5.3 μg/g | 1,100 μg/L |

A method of degrading TNT using isolate CR-1 is as follows. A solution is prepared containing a mineral salts solution, usually NATE, and about 20 mg/L to about 200 rag/L, usually about 50 mg/L, TNT. Isolate CR-1 is grown on a suitable medium, usually Trypticase Soy Agar, for generally 1-2 days at about 15° C. to about 40° C., usually about 30° C., and harvested dry. Isolate CR-1 is added to the TNT solution at a concentration of about $10^3$/ml to about $10^9$/ml, usually about $10^6$/ml, followed by incubation at about 15° C. to about 40° C., usually about 30° C., to degrade the TNT.

A typical NATE solution is generally prepared using the following materials:

Solution A (10X stock)
  10 g/L $MgSO_4 \cdot 7H_2O$
  2 g/L $CaCl_2$
  10 g/L $KNO_3$
  1 g/L $NH_4Cl$ Solution B (100X stock)
  5 mg/L $CuSO_4 \cdot 5H_2O$
  1 mg/L $H_3BO_3$
  1 mg/L $MnSO_4$ or 0.76 mg/L $MNSO_4 \cdot 1 H_2O$
  7 mg/L $ZnSO_4$
  1 mg/L $MoO_3$
  1 mg/L $CoCl_2 \cdot 6H_2O$ Phosphate Buffer
  8.5 g $KH_2PO_4$ and 6.5 g $K_2HPO_4$ in 300 ml Iron Chloride
  0.027 g/100 ml $FeCl_3$ To prepare a typical NATE media, 100 ml of solution B is added to 1 liter of solution A, resulting in a 10X NATE solution which can be autoclaved (sterilized). After cooling, the sterilized 10X NATE solution is diluted 1:10 with sterile water to obtain a 1X NATE solution. To 1 liter of the 1X NATE solution is added 20 ml filter sterilized phosphate buffer and add 10 ml of filter sterilized $FeCl_3$ to obtain the finished NATE media.

EXAMPLE IV

TNT was dissolved in water and diluted 1:1 with NATE media in a test bottle, resulting in a solution containing about 50 mg/L TNT. Isolate CR-1 was grown on Trypticase Soy Agar for 1-2 days at 30° C. and then harvested dry. Isolate CR-1 was then added to the TNT/NATE solution at a concentration of $10^6$/ml, followed by incubation at 30° C. until the solution had attained a stable yellow-orange color. A control for this experiment was similar to the test, with the organisms killed by autoclaving prior to addition to the test bottle. Each bottle was analyzed by high pressure liquid chromatography (HPLC) and showed a marked decrease in TNT levels by the live bacteria. Small quantities of 4-amino-2,6-dinitrotoluene (4-ADNT), one of the metabolites associated with the degradation of TNT, were detected as indicated in Table 3.

TABLE 3

CONCENTRATION OF TNT AND ITS METABOLITES AFTER INCUBATION WITH BACTERIA ISOLATE CR-1

| Isolate | TNT, mg/L | 4-ADNT, mg/L |
|---|---|---|
| CR-1 (5 minutes) | 36 | 0 |
| CR-1 (24 hours) | 10 | 0.3 |
| Control (24 hours) | 48 | 0 |

EXAMPLE VI

Additional experiments were then undertaken using a similar protocol as previously mentioned except that the saturated TNT solution now contained $^{14}$C-labeled TNT. Most of the $^4$C-TNT was associated with the cell pellet. Further analysis of the cell pellet showed no detectable TNT present. TNT metabolites were detected in small amounts in the test bottles. Results are shown in Tables 4 and 6.

TABLE 4

| | % $^{14}$C-TNT per fraction | | |
|---|---|---|---|
| EXPERIMENT | Cell Pellet | $CO_2$ | Soluble |
| 1 | 70 | 1 | 29 |
| 2 | 66 | 2 | 32 |
| Control | 6 | 4 | 90 |

TABLE 5

| | % TNT and Metabolites in Cell Pellet | | |
|---|---|---|---|
| EXPERIMENT | TNT | 2-ADNT | 4-ADNT |
| 1 | 0.0 | 0.009 | 0.04 |
| 2 | 0.0 | 0.005 | 0.05 |
| Control | 0.0 | 0.000 | 0.00 |

Deposit of Microorganisms

The applicants, in accordance with the provisions of the Budapest treaty on the international recognition of the deposit of microorganisms for the purposes of patent procedure under the Budapest Treaty, did deposit samples of Isolate NAP-1, Isolate 13, Isolate CR-1, and Isolate 1S with the American Type Culture Collection (ATCC), 12301 Parklawn Drive, Rockville, Ma. 20852, U.S.A. on Aug. 20, 1993 and assigned ATCC deposit reference Numbers 77526, 77527, 77528, and 77529, respectively. Each culture is hereby irrevocably and without restriction or condition released to the public upon the issuance of letters patent herefor.

While there has been shown and described what are at present considered the preferred embodiments of the invention, it will be obvious to those skilled in the art that various changes and modifications can be made therein without departing from the scope of the inventions defined by the appended claims.

What is claimed is:

1. A method of degrading napalm B comprising the steps of:
   a. providing a culture of a bacterium comprising an intra-amoebic isolate possessing all the identifying characteristics of American Type Culture Collection Deposit Number 77529, a mutant of said isolate possessing all the identifying characteristics thereof, or mixtures thereof;
   b. deriving an aqueous dispersant solution from said culture;
   c. contacting napalm B with a sufficient amount of said dispersant solution to emulsify said napalm B producing emulsified napalm B; and,
   d. contacting said emulsified napalm B with a sufficient amount of at least one other intra-amoebic isolate possessing all the identifying characteristics of American Type Culture Collection Deposit Numbers 77526, and ATCC No. 77527, a mutant thereof possessing all the identifying characteristics thereof, or mixtures thereof, to degrade said emulsified napalm B; and,
   e. degrading said emulsified napalm B.

2. A method according to claim 1 wherein said dispersant solution is diluted 1:10 with water after step b, and wherein, in step c, said napalm B is added to said diluted dispersant solution in an amount in the range of about 5% to about 20%.

3. A method according to claim 2 wherein said amount of napalm B is about 10%.

4. A method according to claim 1 wherein said other intra-amoebic isolate is a supernatant bacterial preparation containing about $10_3$/ml to about $10_8$/ml of said other isolate.

5. A method according to claim 4 wherein said supernatant bacterial preparation contains about $10^5$/ml of said other isolate.

6. A method according to claim 1 wherein, in step d, said other intra-amoebic isolate is added to said emulsified napalm B in a ratio in the range of about 3:1 to about 1:3.

7. A method according to claim 6 wherein said ratio is about 1:1.

8. A method according to claim 1 wherein step d is carried out at a temperature in the range of about 15° C. to about 40° C.

9. A method according to claim 16 wherein said temperature is about 30° C.

* * * * *